United States Patent
Moody et al.

(10) Patent No.: US 8,853,429 B2
(45) Date of Patent: *Oct. 7, 2014

(54) PROCESS AND INTERMEDIATE COMPOUNDS USEFUL IN THE PREPARATION OF STATINS

(71) Applicant: Redx Pharma Limited, Manchester (GB)

(72) Inventors: David John Moody, Fife (GB); Jonathan William Wiffen, County Down (GB)

(73) Assignee: Redx Pharma Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/951,650

(22) Filed: Jul. 26, 2013

(65) Prior Publication Data

US 2013/0345429 A1    Dec. 26, 2013

Related U.S. Application Data

(63) Continuation of application No. 13/599,606, filed on Aug. 30, 2012, now Pat. No. 8,519,164, which is a continuation of application No. 11/721,858, filed as application No. PCT/GB2005/004541 on Nov. 28, 2005, now Pat. No. 8,278,467.

(30) Foreign Application Priority Data

Dec. 16, 2004   (GB) ................................ 0427491.6

(51) Int. Cl.
| | |
|---|---|
| C07D 215/38 | (2006.01) |
| C07D 405/06 | (2006.01) |
| C07D 257/04 | (2006.01) |
| C07D 309/30 | (2006.01) |
| C07D 209/24 | (2006.01) |
| C07C 51/09 | (2006.01) |
| C07D 309/10 | (2006.01) |
| C07D 215/14 | (2006.01) |
| C07B 41/08 | (2006.01) |

(52) U.S. Cl.
CPC .............. *C07B 41/08* (2013.01); *C07D 405/06* (2013.01); *C07D 257/04* (2013.01); *C07D 309/30* (2013.01); *C07D 209/24* (2013.01); *C07C 51/09* (2013.01); *C07D 309/10* (2013.01); *C07D 215/14* (2013.01)
USPC ....................................... 549/416; 558/172

(58) Field of Classification Search
USPC .......................................... 549/416; 558/172
See application file for complete search history.

(56) References Cited

U.S. PATENT DOCUMENTS

| | | | |
|---|---|---|---|
| 4,474,971 A | 10/1984 | Wareing | |
| 4,625,039 A | 11/1986 | Jewell, Jr. et al. | |
| 4,677,211 A * | 6/1987 | Jewell et al. ................. | 548/491 |
| 5,159,104 A | 10/1992 | Dabora et al. | |
| 5,795,749 A | 8/1998 | Wong et al. | |
| 6,689,748 B1 | 2/2004 | Theoharides | |
| 8,278,467 B2 * | 10/2012 | Moody et al. ................. | 549/416 |
| 8,519,164 B2 * | 8/2013 | Moody et al. ................. | 549/416 |

FOREIGN PATENT DOCUMENTS

| | | |
|---|---|---|
| WO | WO 88/05296 A1 | 7/1988 |
| WO | WO 00/49014 A1 | 8/2000 |
| WO | WO 01/85702 A1 | 11/2001 |
| WO | WO 2005/030758 A1 | 4/2005 |
| WO | WO 2005/079790 A1 | 9/2005 |
| WO | WO 2005/092867 A2 | 10/2005 |

OTHER PUBLICATIONS

Hughes "Steroselective Approaches to the Hexahydronaphthalnes Portions of the HMG-CoA Reductase Inhibitors", *Sel. Org. React. Database* 2 pages (2001) Abstract Only.

Suckling "Use and limitations of models and modelling in medicinal chemistry", *Comprehensive Medicinal Chem.* 4:83-104 (1990) Abstract Only.

(Continued)

*Primary Examiner* — D M Seaman
(74) *Attorney, Agent, or Firm* — Myers Bigel Sibley & Sajovec, P.A.

(57) ABSTRACT

There is provides a process for the preparation of a compound of formula (7): wherein R is an optionally substituted hydrocarbyl group or an optionally substituted heterocyclic group; provides that R is not a compound of Formula (a): wherein $R^a$ represents an alkyl group, such as a $C_{1-16}$ alkyl group, and preferably an isopropyl group; $R^b$ represents an aryl group, preferably a 4-fluorophenyl group; $R^c$ represents hydrogen, a protecting group or an alkyl group, such as a $C_{1-16}$ alkyl group, and preferably a methyl group; and Rd represents hydrogen, a protecting group or a $SO_2R^e$ group where $R^e$ is an alkyl group, such as a $C_{1-16}$ alkyl group, and preferably a methyl group.

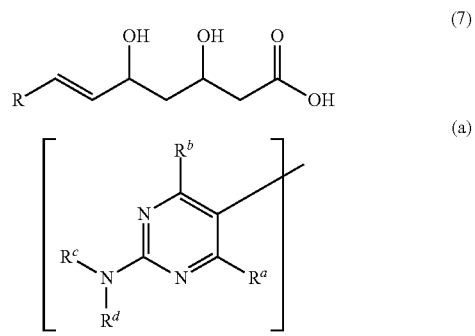

18 Claims, No Drawings

(56) References Cited

OTHER PUBLICATIONS

Fawzi et al., CA 110:237145, abstract only of WO 8805296 (1988).
Pfefferkorn, CA 149:576312, abstract only of Art of Drug synthesis, pp. 169-182 (2007).
Barth et al. "Towards a New Type of HMG-CoA Reductase Inhibitor" *Tetrahedron* 46(19):6731-6740 (1990).
Beck et al, "Synthesis and Biological Activity of New HMG-CoA Reductase Inhibitors. 1. Lactones of Pyridine- and Pyrimidine-Substituted 3,5-Dihydroxy-6-heptenoic (-heptanoic) Acids" *J. Med. Chem.* 33:52-60 (1990).
International Search Report and Written Opinion for PCT/GB2005/00451; Feb. 27, 2006.
Rosen et al. Synthetic and Biological Studies of Compactin and Related Compounds. 2. Synthesis of the Lactone Moiety of Compactin[1] *J. Org. Chem.* 49(21):3994-4003 (1984).
Sawamura et al. "Conversion of Alkyl Halides into Alcohols Using a Near Stoichiometric Amount of Molecular Oxygen: An Efficient Route to $^{18}$O- and $^{17}$O-Labeled Alcohols" *Synlett* 7:801-802 (1997).
Wade et al. "A Useful Route to Optically Active 4-Oxygenated 4,5-ihyroisoxazoles" *J. Org. Chem.* 59:7199-7200 (1994).
"Organic Chemistry" *Shandong Education Press* p. 187 (1985).
Office Action corresponding to Chinese Patent Application No. 200580047969.3 dated Mar. 8, 2010.
Hiyama et al. "Synthesis of Artificial HMG-CoA Reductase Inhibitors Based on the Olefination Strategy", *Bull. Chem. Soc. Jpn.* 68:364-372 (1995).
Tempkln et al, "Asymmetric Synthesis of 3,5-Dihydroxy-6(*E*)-heptenoate-containing HMG-CoA Reductase Inhibitors", *Tetrahedron* 53(31):10659-10670 (1997).
Minami et al. "A Novel Enantioselective Syntehsis of HMG Co-A Reductase Inhibitor NK-104 and a Related Compound", *Tetrahedron Letters* 33(49):7525-7526 (1992).

* cited by examiner

PROCESS AND INTERMEDIATE COMPOUNDS USEFUL IN THE PREPARATION OF STATINS

RELATED APPLICATION

This application is a continuation application of U.S. application Ser. No. 13/599,606, filed on Aug. 30, 2012, now allowed, which is a continuation application of U.S. application Ser. No. 11/721,858, filed on Jun. 23, 2009, issued on Oct. 2, 2012 as U.S. Pat. No. 8,278,467, which claims priority to and is a 35 U.S.C. §371 national stage application of PCT Application No. PCT/GB2005/004541, filed on Nov. 28, 2005, which claims priority from Great Britain Application No. 0427491.6, filed on Dec. 16, 2004, the disclosures and content of each of which are incorporated by reference herein in their entireties.

The present invention concerns a process and intermediate compounds useful in the preparation of statins.

According to the present invention there is provide a process for the preparation of a compound of formula (7):

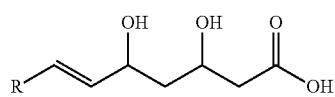

(7)

wherein
R is a an optionally substituted hydrocarbyl group or an optionally substituted heterocyclic group;
provided that R is not a compound of Formula (a):

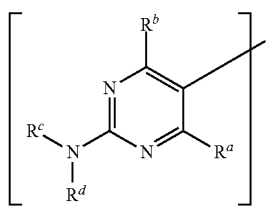

wherein
$R^a$ represents an alkyl group, such as a $C_{1-6}$ alkyl group, and preferably an isopropyl group;
$R^b$ represents an aryl group, preferably a 4-fluorophenyl group;
$R^c$ represents hydrogen, a protecting group or an alkyl group, such as a $C_{1-6}$ alkyl group, and preferably a methyl group; and
$R^d$ represents hydrogen, a protecting group or a $SO_2R^e$ group where $R^e$ is an alkyl group, such as a $C_{1-6}$ alkyl group, and preferably a methyl group,
which comprises
a) hydroxylating a compound of formula (1):

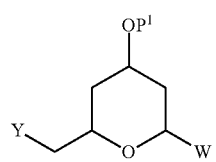

wherein Y represents a halo group, preferably Cl or Br; $P^1$ represents hydrogen or a protecting group, and W represents =O or —$OP^2$, in which $P^2$ represents hydrogen or a protecting group,
to give a compound of formula (2):

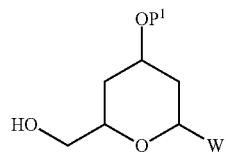

b) oxidising the compound of formula (2) to give a compound of formula (3):

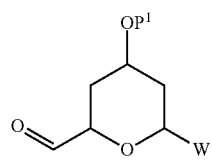

c) coupling the compound of formula (3) with a compound of formula (4):

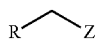

wherein Z represents $(PR^{11}R^{12})^+X^-$ or $P(=O)R^{11}R^{12}$ in which X is an anion and $R^{11}$ and $R^{12}$ each independently is an alkyl, aryl, alkoxy or aryloxy group, preferably a phenyl group,
to give a compound of formula (5):

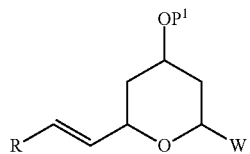

d) when W represents —$OP^2$, removing any $P^2$ protecting group and oxidising the compound of formula (5) to give a compound of formula (6):

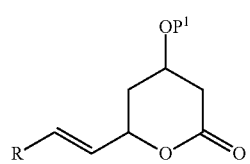

and
e) subjecting the compound of formula (5) when W represents =O, or compound of formula (6) to ring-opening, removal of any $P^1$ protecting groups, and optionally removing any additional protecting groups to give a compound of formula (7).

In step (e), any $P^1$ protecting groups and any additional protecting groups may be removed individually or together and prior to ring opening, during ring opening or after ring opening of the compounds of formula (5) or (6).

Preferably, there is provided a process for the preparation of a compound of formula (7):

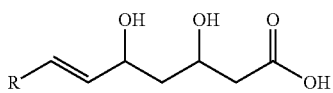

wherein
R is a group selected from

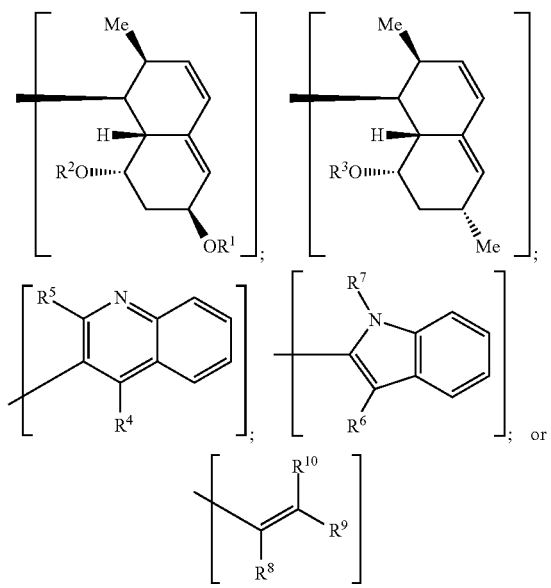

and wherein
R¹ represents hydrogen, a protecting group or an optionally substituted hydrocarbyl group, preferably an alkyl group, such as a $C_{1-6}$ alkyl group;
R² represents an optionally substituted acyl group, preferably an alkanoyl group, such as $C_{1-8}$ alkanoyl group, and preferably a —C(O)CH(Me)CH₂CH₃ or —C(O)C(Me)₂CH₂CH₃ group;
R³ represents an optionally substituted acyl group, preferably an alkanoyl group, such as $C_{1-8}$ alkanoyl group, and preferably a —C(O)CH(Me)CH₂CH₃ or —C(O)C(Me)₂CH₂CH₃ group;
R⁴ represents an optionally substituted hydrocarbyl group, preferably an optionally substituted aryl group, more preferably a 4-fluorophenyl group;
R⁵ represents an optionally substituted hydrocarbyl group, preferably an optionally substituted alkyl group, such as a $C_{1-6}$ alkyl group, and more preferably a cyclopropyl group;
R⁶ represents an optionally substituted hydrocarbyl group, preferably an optionally substituted aryl group, more preferably a 4-fluorophenyl group;
R⁷ represents an optionally substituted hydrocarbyl group, preferably an optionally substituted alkyl group, such as a $C_{1-6}$ alkyl group, and more preferably an isopropyl group;
R⁸ represents an optionally substituted hydrocarbyl group, or optionally substituted heterocyclic group, preferably an optionally substituted aryl or an optionally substituted aromatic heterocyclic group, more preferably a methyltetrazoyl group;
R⁹ represents an optionally substituted hydrocarbyl group, preferably an optionally substituted aryl group, more preferably a 4-fluorophenyl group;

R¹⁰ represents an optionally substituted hydrocarbyl group, preferably an optionally substituted aryl group, more preferably a 4-fluorophenyl group,
which comprises
a) hydroxylating a compound of formula (1):

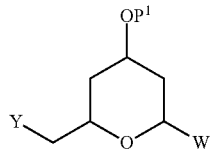

wherein Y represents a halo group, preferably Cl or Br; P¹ represents hydrogen or a protecting group, and W represents =O or —OP², in which P² represents hydrogen or a protecting group,
to give a compound of formula (2):

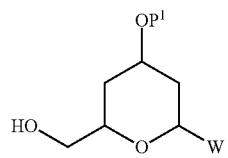

b) oxidising the compound of formula (2) to give a compound of formula (3):

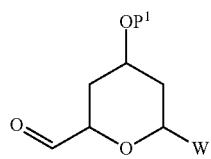

c) coupling the compound of formula (3) with a compound of formula (4):

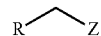

wherein Z represents (PR¹¹R¹²)⁺X⁻ or P(=O)R¹¹R¹² in which X is an anion and R¹¹ and R¹² each independently is an alkyl, aryl, alkoxy or aryloxy group, preferably a phenyl group,
to give a compound of formula (5):

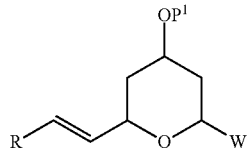

d) when W represents —OP², removing any P² protecting group and oxidising the compound of formula (5) to give a compound of formula (6):

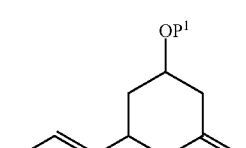

and
e) subjecting the compound of formula (5) when W represents =O, or compound of formula (6) to ring-opening, removal of any P¹ protecting groups, and optionally removing any additional protecting groups to give a compound of formula (7).

In step (e), any $P^1$ protecting groups and any additional protecting groups may be removed individually or together and prior to ring opening, during ring opening or after ring opening of the compounds of formula (5) or (6).

Further, compounds of formula (8):

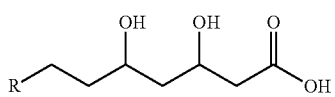

wherein R is as defined above for $R^7$,
may be obtained by reduction of a compound of Formula (7) or, alternatively
a compound of Formula (5) or (6) may be reduced to a corresponding compound of Formula (9) or (10).

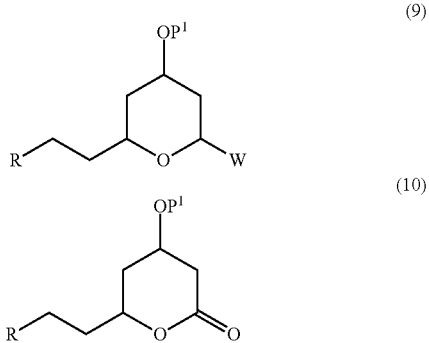

and then the compound of formula (9) when W represents —$OP^2$ may be converted to a compound of formula (10) by removing any $P^2$ protecting group and oxidising the compound of formula (9) to give a compound of formula (10), and then the compound of formula (9), when W represents =O, or a compound of formula (10) may be ring-opened, any $P^1$ protecting groups, and optionally removing any additional protecting groups to give a compound of formula (8). Any $P^1$ protecting groups and any additional protecting groups may be removed individually or together and prior to ring opening, during ring opening or after ring opening of the compounds of formula (9) or (10).

Protecting groups which may be represented by $P^1$ and $P^2$ include alcohol protecting groups, examples of which are well known in the art. Particular examples include tetrahydropyranyl, benzyl and methyl groups. Preferred protecting groups are silyl groups, for example triaryl- and especially trialkylsilyl groups. Especially preferred examples are trimethylsilyl, t-butyldimethylsilyl and t-butyldiphenyl groups.

Protecting groups which may be represented by $P^1$ and $P^2$ may be the same or different. When the protecting groups $P^1$ and $P^2$ are different, advantageously this may allow for the selective removal of only $P^1$ or $P^2$. Preferably, when the protecting groups $P^1$ and $P^2$ are different, $P^1$ is a silyl group and $P^2$ is a methyl group.

Protecting groups which may be represented by $R^1$ include alcohol protecting groups, examples of which are well known in the art.

Protecting groups which may be represented by $R^c$ and $R^d$ include amine protecting groups, examples of which are well known in the art. Particular examples include benzyl groups, carbamates (such as CBZ, Boc, Fmoc), phosphate, thiophosphate, silyl groups and, when $R^c$ and $R^d$ together are a single protecting group, an imine group.

Hydrocarbyl groups which may be represented by R, $R^1$ and $R^3$ independently include alkyl, alkenyl and aryl groups, and any combination thereof, such as aralkyl and alkaryl, for example benzyl groups.

Alkyl groups which may be represented by R, $R^a$, $R^c$, $R^d$, $R^1$ and $R^{4-10}$ include linear and branched alkyl groups comprising up to 20 carbon atoms, particularly from 1 to 7 carbon atoms and preferably from 1 to 5 carbon atoms. When the alkyl groups are branched, the groups often comprising up to 10 branch chain carbon atoms, preferably up to 4 branch chain atoms. In certain embodiments, the alkyl group may be cyclic, commonly comprising from 3 to 10 carbon atoms in the largest ring and optionally featuring one or more bridging rings. Examples of alkyl groups which may be represented by R, $R^a$, $R^c$, $R^d$, $R^1$ and $R^{4-10}$ include methyl, ethyl, propyl, 2-propyl, butyl, 2-butyl, t-butyl and cyclohexyl groups.

Alkenyl groups which may be represented by R, $R^1$ and $R^{4-10}$ include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups.

Aryl groups which may be represented by R, $R^b$, $R^1$ and $R^{4-10}$ may contain 1 ring or 2 or more fused rings which may include cycloalkyl, aryl or heterocyclic rings. Examples of aryl groups which may be represented by $R^1$, $R^b$ and $R^{4-10}$ include phenyl, tolyl, fluorophenyl, chlorophenyl, bromophenyl, trifluoromethylphenyl, anisyl, naphthyl and ferrocenyl groups.

Heterocyclic groups which may be represented by R, $R^1$ and $R^{4-10}$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. When any of R, $R^1$ or $R^{4-10}$ represents or comprises a heterocyclic group, preferably attachment is provided through a carbon atom in the R, $R^1$ or $R^{4-10}$ group. Examples of heterocyclic groups which may be represented by R, $R^1$ and $R^{4-10}$ include pyridyl, pyrimidyl, pyrrolyl, thiophenyl, furanyl, indolyl, quinolyl, isoquinolyl, imidazoyl, triazoyl and tetrazoyl groups.

When any of R, $R^1$ and $R^{4-10}$ is a substituted hydrocarbyl group, the substituent(s) should be such so as not to adversely affect the rate or selectivity of any of the reaction steps or the overall process. Optional substituents include halogen, cyano, nitro, hydroxy, amino, thiol, acyl, hydrocarbyl, heterocyclyl, hydrocarbyloxy, mono or di-hydrocarbylamino, hydrocarbylthio, esters, carbamates, carbonates, amides, sulphonyl and sulphonamido groups wherein the hydrocarbyl groups are as defined for $R^1$ above. One or more substituents may be present. Examples of $R^1$ and $R^{4-10}$ groups having more than one substituent present include —$CF_3$ and —$C_2F_5$.

Hydroxylation of compounds of formula (1) can be achieved by methods known in the art for displacing a halo group with a hydroxide source. Preferably, the process comprises contacting the compound of formula (1) with a source of hydroxide. Hydroxide sources include hydroxide salts, especially ammonium or alkali metal hydroxides, particularly lithium, sodium or potassium hydroxide, and various aqueous media such as water in the presence of basic media such as N-methylpyrrrolidinone, HMPA, $Al_2O_3$, $CaCO_3$, $Na_2CO_3$, $K_2CO_3$ or $KO_2$/18-crown-6, silver salts such as AgNO₃ or Ag₂O, or oxidants such perbenzoic acid. A particularly preferred process comprises contacting the compound of formula (1) with 5 molar equivalents of KOH in the presence of dimethylsulfoxide solvent at a temperature of, for example, about 50° C.

Alternatively, hydroxylation may be achieved by first displacing the halogen with a leaving group such as acetate, triflate or sulphate optionally in the presence of a silver salt, then displacing the leaving group with a hydroxide source. A particularly preferred process comprises contacting the compound of formula (1) with 3 molar equivalents of NaOAc in the presence of dimethylformamide solvent and tetra-n-butylammonium chloride at a temperature of, for example, about 100° C., isolating the acetyl compound and contacting with potassium carbonate in the presence of methanol solvent and at a temperature of, for example, about 0° C.

Oxidation of compounds of formula (2) can be achieved using oxidation systems known in the art for the oxidation of alcohols, especially those known in the art for the oxidation of primary alcohols. Examples include oxidation with Dess-Martin periodinane, bromine, Swern oxidation or various metal based oxidations such as Fetizon reagent, manganate based reagents, and chromate based reagents such as Collins reagent. Swern oxidation is preferred. When Swern oxidation is employed, preferred conditions comprise the use of dimethyl sulphoxide and oxalyl chloride or bromine in a solvent such as dichloromethane or dichlormethane/THF mixtures, at reduced temperature, such as from 0 to −100° C., preferably −50 to −80° C. Preferably, reagents are added at reduced temperature, such as −30 to −80° C., and then once all reagents are added, the reaction mixture is allowed to warm to 15 to 20° C.

The coupling of the compound of formula (3) with the compound of formula (4) may employ conditions analogous to those given in Bull. Chem. Soc. Japan 1995, 68, 364-372, Tet. Lett. 1992, 33(49), 7525-75226, Tetrahedron 1997, 53(31) 10659-10670 and WO01/85702. The conditions preferably comprise reacting the compounds of formula (3) and (4) in a hydrocarbon solvent, such as THF, toluene or cyclohexane, or mixtures thereof, optionally in the presence of a base, followed by contact with aqueous acid, such as aqueous HCl.

Alkyl, aryl, alkoxy or aryloxy groups which may be represented by $R^{11}$ and $R^{12}$ include $C_{1-6}$alkyl groups, such as methyl and ethyl groups, $C_{6-12}$aryl groups, such phenyl, tolyl or naphthyl, $C_{1-6}$alkoy groups, such as ethoxy groups, and $C_{6-12}$aryloxy groups such as phenoxy groups.

Anions which may be represented by X include halide.

Z preferably is $P(=O)R^{11}R^{12}$ where $R^7$ and $R^8$ each independently is an alkyl, aryl, alkoxy or aryloxy group, preferably a phenyl group.

When W represents $OP^2$, the protecting group may be removed to form a hydroxy group by methods known in the art for the removal of the given protecting group. For example, silyl protecting groups may be removed by contact with a source of fluoride ion, such as tetrabutylammonium fluoride.

Oxidation of compounds formed by deprotection of compounds wherein W represents —$OP^2$ may employ conditions known in the art for the oxidation of pyranols to pyranones, and include those given in "Comprehensive Organic Transformations", R. C. Larock, $2^{nd}$ Ed (1999) p 1670, published by Wiley VCH, incorporated herein by reference. Preferred oxidation systems include Ag₂CO₃/Celite, especially Celite J2, bromine or Swern.

Ring opening of the compounds of formula (5), when W represent =O or formula (6) may employ conditions known in the art for ring opening of a pyranone. Preferably, the ring is opened by contact with a base, such as sodium hydroxide. Conveniently, polar solvents are employed, for example methanol, acetonitrile, tetrahydrofuran or mixtures thereof.

Remaining protecting groups may be removed by methods known in the art for the removal of the given protecting group. For example, silyl protecting groups may be removed by contact with a source of fluoride ion, such as tetrabutylammonium fluoride.

It will also be recognised that compounds of formulae (2), (3) and (5) may also be subjected to oxidation (when W represents —OH) or deprotection and oxidation (when W represents (—O-protecting group) to form the corresponding compound wherein W represents =O.

Reduction of the compounds of formula (5), (6) or (7) may employ conditions known in the art for the reduction of double bonds. For example, hydrogenation using hydrogen gas in the present of transition metals or transition metal catalysts such as hydrogen in the presence of group VIII metal or metal catalyst, especially Ru, Rh, Pd, Ir or Pt metals or metal based catalysts.

Preferred compounds of formula (1) are compounds of formula:

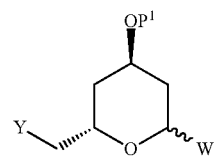

wherein W, $P^1$ and Y are as previously described.

Preferred compounds of formula (2) are compounds of formula:

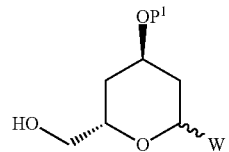

wherein W and $P^1$ are as previously described.

Preferred compounds of formula (3) are compounds of formula:

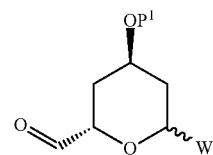

wherein W and $P^1$ are as previously described.

Preferred compounds of formula (5) are of formula:

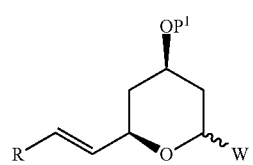

wherein $R^1$, $R^2$, W and $P^1$ are as previously described.

Preferred compounds of formula (6) are of formula:

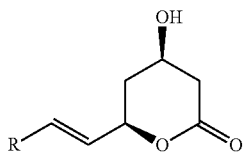

wherein $R^1$ and $R^2$ are as previously described.
Preferred compounds of formula (7) are of formula:

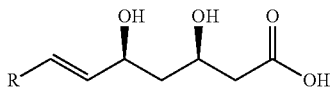

wherein $R^1$ and $R^2$ are as previously described.

Compounds of formula (7) are advantageously converted to pharmaceutically acceptable salts, especially their calcium salts.

Compounds of formula (4) are advantageously prepared by analogy to the methods given in Bull. Chem. Soc. Japan 1995, 68, 364-372, Tet. Lett. 1992, 33(49), 7525-75226, Tetrahedron 1997, 53(31) 10659-10670, WO00/49014 and WO01/85702. Particularly preferred compounds of formula (4) are compounds of formula:

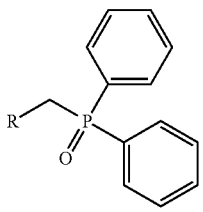

Compounds of formula (1) are advantageously prepared by enzyme catalysed condensation of acetaldehyde and 2-haloacetaldehyde, for example using the method given in U.S. Pat. No. 5,795,749.

Compounds of formula (5) and (9) when W is $OP^2$ are further aspects of the present invention.

The invention is illustrated by the following examples.

EXAMPLE 1

Preparation of Chlorolactol methyl acetal ((2S,4R)-2-(chloromethyl)-6-methoxytetrahydro-2H-pyran-4-ol), a compound of Formula 1 where Y=Cl, $P^1$=H and W=—$OP^2$, in which $P^2$=Me Crude chlorolactol (15 g) was dissolved in methanol (150 ml) and heated to 40° C. for 2 hours in the presence of 0.1 ml sulphuric acid. The solvent was removed by rotary evaporation to afford the product as a dark brown flowing oil. The product was dissolved in DCM and washed with sodium bicarbonate solution. The solvent was removed by rotary evaporation to afford the product as a dark brown flowing oil, which was purified by column chromatography (16.1 g) containing a mixture of anomers m/z 179, 149 and 113; $^1$H nmr CDCl$_3$ 3.6-3.7 (m 2H), 4.1 (m 1H), 1.5-1.6 (m 2H), 4.0 (m 1H), 1.3-1.6 (m 2H), 4.9 (m 1H), 3.3 & 3.5 (s 3H); $^{13}$C nmr CDCl$_3$ 32, 36, 45, 55&56, 64, 65, 94.

EXAMPLE 2

Preparation of O-benzyl-chlorolactol methyl acetal ((2S,4R)-4-(benzyloxy)-2-(chloromethyl)-6-methoxytetrahydro-2H-pyran), a compound of Formula 1 where Y=Cl, $P^1$=Bn and W=—$OP^2$, in which $P^2$=Me Chlorolactol methyl acetal (1 g) was dissolved in THF (5 ml) and charged to sodium hydride (0.33 g 60% in mineral oil) in THF (5 ml) at room temperature. Benzyl bromide (1.9 g) was added dropwise and the mass heated to 80° C. for 2 hours. Methanol (2 ml) was added and the mass was partitioned between DCM/water, and was then washed with water. The organic phase was dried and the solvent was removed by rotary evaporation to afford an orange flowing oil (2.1 g), containing a mixture of anomers containing a mixture of anomers. m/z 270; 238; 203; 132; 91; $^1$H nmr CDCl$_3$ 1.6-2.0 (m 4H), 3.4 & 3.5 (s 3H), 3.6 (m 2H), 3.8 (m 1H), 4.0 (m 1H), 4.5 (m 2H), 4.7 (m 1H), 7.3-7.5 (m 5H); $^{13}$C nmr CDCl$_3$ 32&33, 46, 55&56, 58, 66, 74, 96&98, 128-131.

EXAMPLE 3

Preparation of Hydroxy-O-benzyl-lactol methyl acetal ([(2R,4R)-4-(benzyloxy)-6-methoxytetrahydro-2H-pyran-2-yl]methanol), a compound of Formula 2 where $P^1$=Bn and W=—$OP^2$, in which $P^2$=Me Preparation of the Acetate Intermediate:

To a 3-liter three necked round bottomed flask flushed with dry nitrogen the O-benzyl-chlorolactol methyl acetal (30 g) was charged into dry N-methylpyrollidinone (756 mls). Anhydrous tetrabutylammonium acetate (102.57 g) was also charged to the solution. The reaction mixture was then heated at 100° C. for 24 hours. The reaction mixture was sampled at routine intervals and directly analysed by tlc and gc/ms.

The black solution was then diluted with water (150 mls) and extracted with ethyl acetate (3×1500 mls). The combined upper organic layer was then washed with water (3×1500 mls). The aqueous portion showed no product content at this point. The layers were then separated, dried, (Na$_2$SO$_4$) and the solvent removed in vacuo to yield a black flowing oil (31 g, 95%) containing a mixture of anomers. $^1$H nmr CDCl$_3$ 1.4-1.8 (m 4H), 2.0-2.1 (duplicate s, 3H), 3.4 & 3.5 (s 3H), 3.8 (m 1H), 4.0 (m 1H), 4.1 (m 2H), 4.5 (m, 2H), 4.7-4.9 (m 1H), 7.2-7.3 (m, 5H); $^{13}$C nmr CDCl$_3$ 20.8; 30-35; 55&56; 57&64; 66&68; 69&72; 70&71; 98&99; 127-128 & 138; 170.5; m/z 293, 262, 221, 203, 156, 91 and 43.

Preparation of the Alcohol from the Acetate Intermediate:

To a 50 mls three necked round bottomed flask flushed with dry nitrogen the O-benzyl-chlorolactol methyl acetal acetate (2 g) was charged into dry methanol (10 mls) containing anhydrous potassium carbonate (1 g). The resultant suspension was stirred at 20° C. for 30 minutes. G.C./M.S. showed complete conversion of acetate to alcohol. The solid was filtered off and the solvent removed in vacuo to yield a brown flowing oil containing a mixture of anomers (1.6 g, 93%). $^1$H nmr CDCl$_3$ 1.4-1.8 (m 4H), 3.4 & 3.5 (s 3H), 3.8 (m 1H), 3.9 (m 1H), 4.0 (m 2H), 4.5 (m 2H), 4.7-4.9 (m 1H), 7.2-7.3 (m, 5H); $^{13}$C nmr CDCl$_3$ 30-38; 55&56; 65&66; 65&69; 70&71; 72&73; 99&100; 128 & 140; m/z 252, 221, 189, 163, 114 and 91.

EXAMPLE 4

Preparation of formyl-O-benzyl-lactol methyl acetal (2S,4R)-4-(benzyloxy)-6-methoxytetrahydro-2H-pyran-2-carbaldehyde a compound of Formula 3 where $P^1$=Bn and W=—$OP^2$, in which $P^2$=Me Dess-Martin periodinane reagent (1.91 g) in dichloromethane (50 mls) was charged to a 1000 mls round bottomed flask purged with dry nitrogen. The hydroxy-O-benzyl-lactol methyl acetal (1.0 g) was dissolved in dichloromethane (50 mls) and added to the Dess-Martin periodinane reagent at 20° C. The reaction mixture was then stirred at room temperature for 30 minutes. The reaction was monitored by tlc. The reaction mixture was then diluted with diethyl ether (500 mls) to precipitate the excess reagent. The suspension was then washed with 10% aqueous sodium hydroxide (200 mls). The upper organic layer was then washed with water (250 mls). The upper organic layer was then separated, dried ($Na_2SO_4$) and the solvent removed in vacuo to yield a dark flowing oil as a mixture of anomers (0.8 g).

$^1$H nmr $CDCl_3$ 1.6-1.9 (m 4H), 3.3 & 3.5 (s 3H), 3.7 (m 1H), 3.8 (m 1H), 4.4 (m 2H), 4.7-4.9 (m 1H), 7.2-8.1 (m, 5H), 9.6-9.7 (2×s, 1H).

$^{13}$C nmr $CDCl_3$ 30-38; 55&56; 65&66; 65&69; 70&71; 99&100; 128 & 140; 201.

m/z 250, 221, 189, 163, 143, 117 and 91.

Alternatively, a Swern oxidation can be carried out as illustrated by the following example:

A stirred solution of oxalyl chloride (0.037 cm$^3$, 0.44 mmol) in dichloromethane (4 cm$^3$) under nitrogen was cooled to −78° C. and DMSO was added in one portion. A solution of the alcohol (100 mg, 0.40 mmol) in dichloromethane (1 cm$^3$) was added to the reaction mixture and the reaction mixture stirred at −78° C. for 5 min. Triethylamine (0.272 cm$^3$, 19.8 mmol) was added and the resulting solution was stirred at −78° C. for 25 min and used immediately without isolation or purification. Tlc $r_f$ 0.40 ethyl acetate:hexane (1:1) orange spot with 2,4-dinitrophenylhydrazine stain

EXAMPLE 5

Preparation of a Compound of Formula 5 where $P^1$=Bz and W=—$OP^2$, in which $P^2$=Me The compound of Formula 5 may be obtained by first dissolving 0.21 g of the compound of formula 4 wherein Z=PO(Ph)$_2$ in 10 ml dry THF, cooling to −60° C. and then adding 0.2 ml of a 2M solution of sodium hexamethyldisilazide. After 20 min, a solution of 0.1 g formyl-O-benzyl-lactol methyl acetal in 10 ml dry THF at −30° C. is added. The reaction mixture is then maintained at this temperature for 8 hours and monitored by tlc. The reaction mixture is allowed to slowly warm up to 20° C. Glacial acetic (5 mls) acid is then charged to quench the reaction. Water (5 mls) is also charged to the mixture. The solvent is then removed in vacuo and reconstituted with toluene (15 mls) and water (15 mls). The upper organic layer is then separated and the aqueous layer is then washed with ethyl acetate (15 mls). The combined organics are then dried and the solvent removed in vacuo to yield an oil containing a mixture of isomers, that can be purified by chromatography.

Example 5a, R is

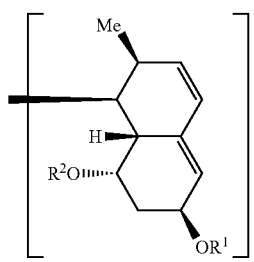

wherein $R^1$ represents hydrogen, a protecting group or a $C_{1-6}$ alkyl group; and $R^2$ represents a —C(O)CH(Me)CH$_2$CH$_3$ or —C(O)C(Me)$_2$CH$_2$CH$_3$ group.

Example 5b, R is

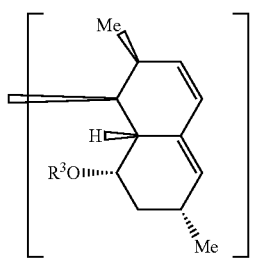

wherein $R^3$ represents a —C(O)CH(Me)CH$_2$CH$_3$ or —C(O)C(Me)$_2$CH$_2$CH$_3$ group.

Example 5c, R is

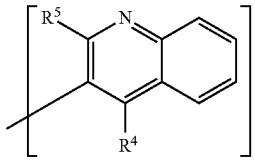

wherein $R^4$ represents a 4-fluorophenyl group; and $R^5$ a $C_{1-6}$ alkyl group, and more preferably a cyclopropyl group.

Example 5d, R is

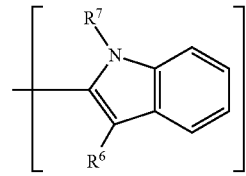

wherein $R^6$ represents a 4-fluorophenyl group; and $R^7$ represents a $C_{1-6}$ alkyl group, and more preferably an isopropyl group.

Example 5e, R is

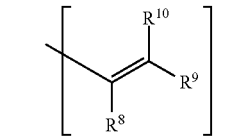

wherein $R^8$ represents a methyltetrazoyl group; $R^9$ represents a 4-fluorophenyl group; and $R^{10}$ a 4-fluorophenyl group.

EXAMPLE 6

Preparation of a Compound of Formula 5 where P¹=H and W=—OP², in which P²=Me

The substituted-ethenyl-OH-lactol methyl acetal may be obtained by reaction of the substituted-ethenyl-O-benzyl-lactol methyl acetal of Example 5(a-e) with TMSI.

EXAMPLE 7

Preparation of a Compound of Formula 5 where P¹=H and W=—OP², in which P²=H

The substituted-ethenyl-OH-lactol may be obtained by treatment of the substituted-ethenyl-OH-lactol methyl acetal of Example 6(a-e) with 0.1; N HCl in methanol.

EXAMPLE 8

Preparation of Lactone, a Compound of Formula 6 where P¹=H

The lactone may be obtained by adding the substituted-ethenyl-OH-lactol of Example 7(a-e) (35 mg, 0.065 mmol) in dichloromethane (0.5 ml) to Dess-Martin periodinane (30 mg, 0.07 mmol) and stirring at room temperature for 2.5 hours. The reaction is partitioned between 1M sodium hydroxide and diethyl ether. The phases are then separated and the organic volume reduced in vacuo to afford the crude product oil.

EXAMPLE 9

Preparation of Hydroxy-Acid (Hydrolysis of Lactone), a Compound of Formula 7

The lactone of Example 8(a-e) (1.1 g) may be ring opened by dissolving in ethanol (10 ml), addition of water (2 ml) and Ca(OH)$_2$ (0.15 g) and warming the suspension to 60° C. for 3 hours. A further 10 ml of warm water is added, before the mixture is allowed to cool slowly to room temperature. The precipitate formed is filtered and dried to give the calcium salt of the hydroxy-acid. The material was identical to an authentic sample by mixed melting point, NMR and mass spectrometry.

The invention claimed is:

1. A process for the preparation of a compound of formula (7):

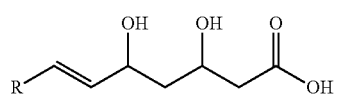

(7)

wherein

R is a substituted or unsubstituted alkenyl or aryl group or any combination thereof, or a substituted or unsubstituted heterocyclic group;

provided that R is not a compound of Formula (a):

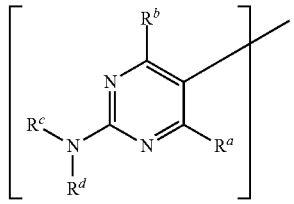

wherein $R^a$ is an alkyl group;
$R^b$ is an aryl group;
$R^c$ is hydrogen, a protecting group or an alkyl group; and
$R^d$ is hydrogen, a protecting group or a SO$_2$R$^e$ group, where R$^e$ is an alkyl group, which comprises:

a) hydroxylating a compound of formula (1):

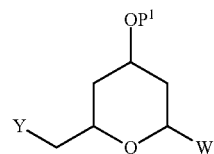

(1)

wherein Y is a halo group, P¹ is hydrogen or a protecting group, and W is —OP², in which P² represents hydrogen or a protecting group, to give a compound of formula (2):

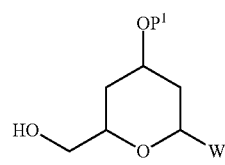

(2)

b) oxidizing the compound of formula (2) to provide a compound of formula (3):

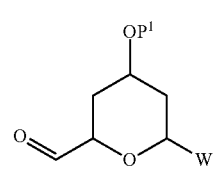

(3)

wherein W represents —OP² or =O, c) the process further comprising forming a compound of formula (2) or (3) in which W represents =O by: oxidizing a compound of formula (2) or (3) wherein P² is hydrogen; or deprotecting and oxidizing a compound of formula (2) or (3) wherein P² is a protecting group;

d) coupling the compound of formula (3) wherein W represents =O with a compound of formula (4):

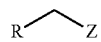

(4)

wherein Z is (PR¹¹R¹²)⁺X⁻ or P(=O)R¹¹R¹², wherein X is an anion and R¹¹ and R¹² each independently is an alkyl, aryl, alkoxy or aryloxy group, to give a compound of formula (5) wherein W represents =O:

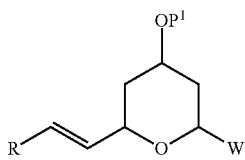

and e) subjecting the compound of formula (5) to ring-opening, removal of any P¹ protecting groups, and optionally removing any additional protecting groups to provide a compound of formula (7).

2. The process of claim 1 wherein Y is Cl or Br.

3. The process of claim 1, wherein R is selected from:

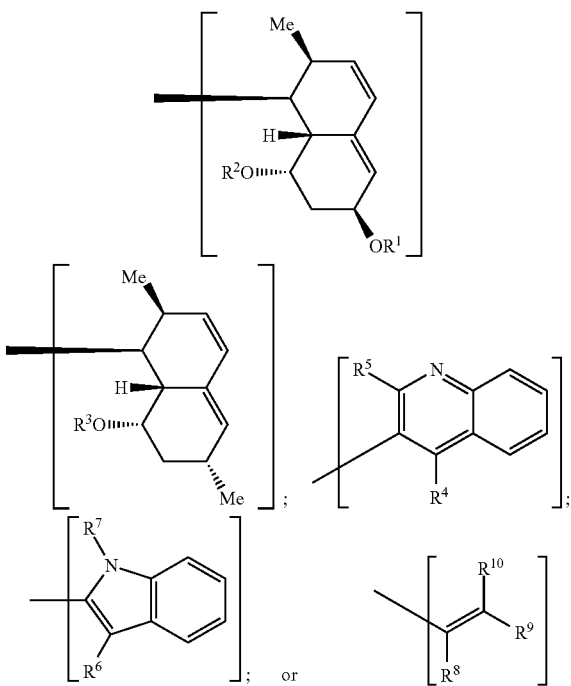

and wherein $R^1$ is a hydrogen, a protecting group or a substituted or unsubstituted hydrocarbyl group;

$R^2$ is a an optionally substituted acyl group;

$R^3$ is an optionally substituted acyl group;

$R^4$ is a substituted or unsubstituted hydrocarbyl group;

$R^5$ is a substituted or unsubstituted hydrocarbyl group;

$R^6$ is a substituted or unsubstituted hydrocarbyl group;

$R^7$ is a substituted or unsubstituted hydrocarbyl group;

$R^8$ is a substituted or unsubstituted hydrocarbyl group, or substituted or unsubstituted heterocyclic group;

$R^9$ is a substituted or unsubstituted hydrocarbyl group;

$R^{10}$ is a substituted or unsubstituted hydrocarbyl group.

4. The process of claim 3, wherein $R^1$ is an alkyl group and/or $R^2$ is an alkanoyl group.

5. The process of claim 4, wherein $R^1$ is a $C_{1-6}$ alkyl group and/or $R^2$ is a $C_{1-8}$ alkanoyl group.

6. The process of claim 5, wherein $R^2$ is a —C(O)CH(Me)CH$_2$CH$_3$ or —C(O)C(Me)$_2$CH$_2$CH$_3$ group.

7. The process of claim 3, wherein $R^3$ is an alkanoyl group.

8. The process of claim 7, wherein $R^3$ is a $C_{1-8}$ alkanoyl group.

9. The process of claim 7, wherein $R^3$ is a —C(O)CH(Me)CH$_2$CH$_3$ or a —, C(O)C(Me)$_2$CH$_2$CH$_3$ group.

10. The process of claim 3, wherein $R^4$ is a substituted or unsubstituted aryl group and/or $R^5$ is a substituted or unsubstituted alkyl group.

11. The process of claim 10, wherein $R^4$ is a 4-fluorophenyl group and/or $R^5$ is a cyclopropyl group.

12. The process of claim 3, wherein $R^6$ is a substituted or unsubstituted aryl group and/or $R^7$ is a substituted or unsubstituted alkyl group.

13. The process of claim 12, wherein $R^6$ is a 4-fluorophenyl group and/or $R^7$ is an isopropyl group.

14. The process of claim 3, wherein $R^8$ is a substituted or unsubstituted aryl or a substituted or unsubstituted aromatic heterocyclic group; $R^9$ is a substituted or unsubstituted aryl group; and/or $R^{10}$ is a substituted or unsubstituted aryl group.

15. The process of claim 14, wherein $R^8$ is a methyltetrazoyl group; $R^9$ is a 4-fluorophenyl group; and/or $R^{10}$ is a 4-fluorophenyl group.

16. The process of claim 3, wherein Y is Cl or Br.

17. The process of claim 1, wherein the process further comprises forming a compound of formula (2) in which W represents =O by: oxidising a compound of formula (2) when W is OP² and P² is hydrogen; or deprotecting and oxidising a compound of formula (2) when W is OP² and P² is a protecting group.

18. The process of claim 1, wherein the process further comprises forming a compound of formula (3) wherein W represents =O by: oxidising a compound of formula (3) when W is —OP² and P² is hydrogen; or deprotecting and oxidising a compound of formula (3) when W is —OP² and P² is a protecting group.

* * * * *

UNITED STATES PATENT AND TRADEMARK OFFICE
CERTIFICATE OF CORRECTION

| | | |
|---|---|---|
| PATENT NO. | : 8,853,429 B2 | Page 1 of 1 |
| APPLICATION NO. | : 13/951650 | |
| DATED | : October 7, 2014 | |
| INVENTOR(S) | : Moody et al. | |

It is certified that error appears in the above-identified patent and that said Letters Patent is hereby corrected as shown below:

In the Claims:
Column 16, Claim 9, Line 20:
  Please correct "or a –, C(O)C(Me)$_2$CH$_2$CH$_3$ group."
    to read -- or a – C(O)C(Me)$_2$CH$_2$CH$_3$ group. --

Signed and Sealed this
Twenty-fourth Day of February, 2015

Michelle K. Lee
*Deputy Director of the United States Patent and Trademark Office*